US009095389B2

(12) United States Patent  (10) Patent No.: US 9,095,389 B2
Graham  (45) Date of Patent: Aug. 4, 2015

(54) BONE FIXATION APPARATUS AND METHOD

(71) Applicant: The Cleveland Clinic Foundation, Cleveland, OH (US)

(72) Inventor: Thomas J. Graham, Beachwood, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 104 days.

(21) Appl. No.: 13/787,910

(22) Filed: Mar. 7, 2013

(65) Prior Publication Data

US 2013/0238034 A1  Sep. 12, 2013

Related U.S. Application Data

(60) Provisional application No. 61/608,185, filed on Mar. 8, 2012.

(51) Int. Cl.
*A61B 17/80* (2006.01)
*A61B 17/84* (2006.01)

(52) U.S. Cl.
CPC ............ *A61B 17/8033* (2013.01); *A61B 17/80* (2013.01); *A61B 17/84* (2013.01); *A61B 17/809* (2013.01)

(58) Field of Classification Search
CPC .... A61B 17/8033; A61B 17/84; A61B 17/80; A61B 17/809; A61B 17/72; A61B 17/7233
USPC .............. 606/70–71, 62, 64–68, 280–299, 60
See application file for complete search history.

(56) References Cited

U.S. PATENT DOCUMENTS

| 5,006,120 | A | * | 4/1991 | Carter | 606/71 |
|---|---|---|---|---|---|
| 5,941,878 | A | * | 8/1999 | Medoff | 606/60 |
| 6,468,278 | B1 | | 10/2002 | Muckter | |
| 6,923,812 | B1 | | 8/2005 | Wellisz | |
| 7,537,604 | B2 | | 5/2009 | Huebner | |
| 7,955,361 | B2 | | 6/2011 | Kitchens | |
| 8,579,945 | B2 | * | 11/2013 | Appenzeller et al. | 606/281 |
| 8,603,091 | B2 | * | 12/2013 | Lutz et al. | 606/70 |
| 2003/0100898 | A1 | | 5/2003 | Wellisz | |
| 2003/0100902 | A1 | | 5/2003 | Wellisz et al. | |
| 2009/0275947 | A1 | | 11/2009 | Graham et al. | |
| 2010/0292696 | A1 | | 11/2010 | Chantelot et al. | |
| 2011/0106081 | A1 | | 5/2011 | Graham et al. | |

* cited by examiner

*Primary Examiner* — Todd Manahan
*Assistant Examiner* — Marcela I Shirsat
(74) *Attorney, Agent, or Firm* — Tarolli, Sundheim, Covell & Tummino

(57) ABSTRACT

A bone fixation apparatus comprises an extramedullary component, an intramedullary component, and a fastener configured and dimensioned to interconnect the extramedullary component and the intramedullary component. The fastener has a head portion and a shank portion. The head portion is configured and dimensioned to be received in the extramedullary component. The shank portion is configured and dimensioned to be received in the intramedullary component. The fastener has a first longitudinal axis extending through both the head portion and the shank portion. The extramedullary component has a second longitudinal axis. The extramedullary component also includes an elongated surface defining an opening through which the shank portion of the fastener passes when the shank portion is received in the intramedullary component. The opening has a V shape. The V shape is oriented transverse to the first longitudinal axis and to the second longitudinal axis.

12 Claims, 3 Drawing Sheets

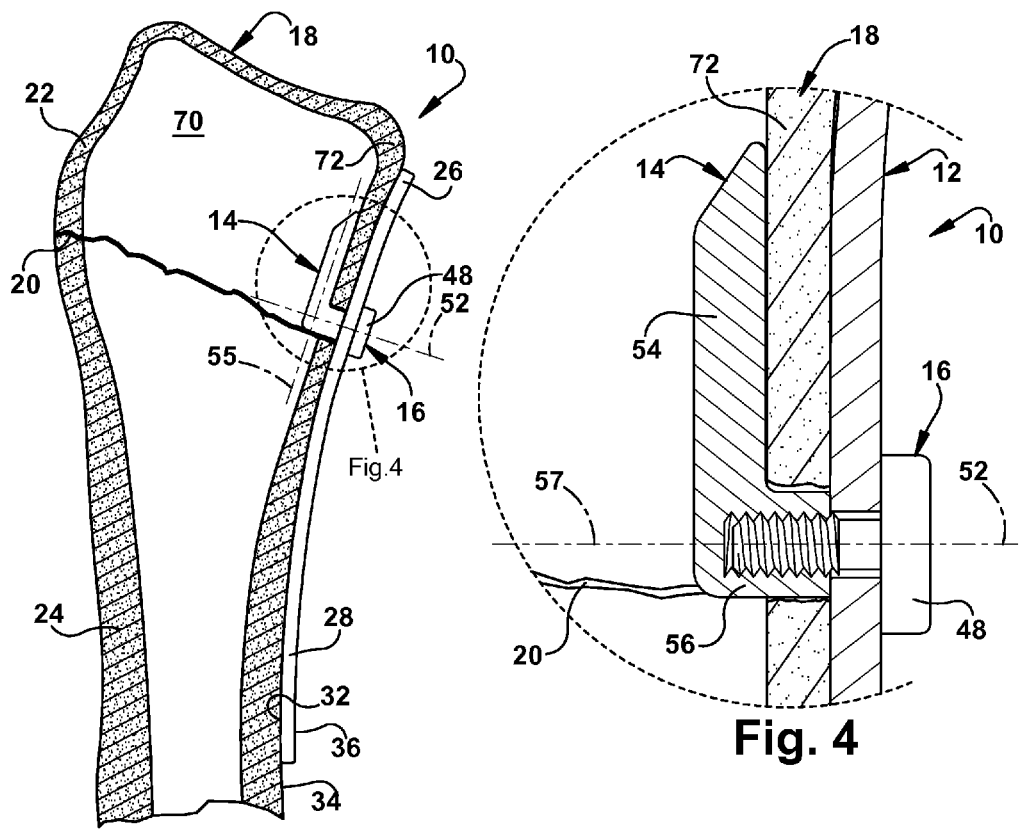
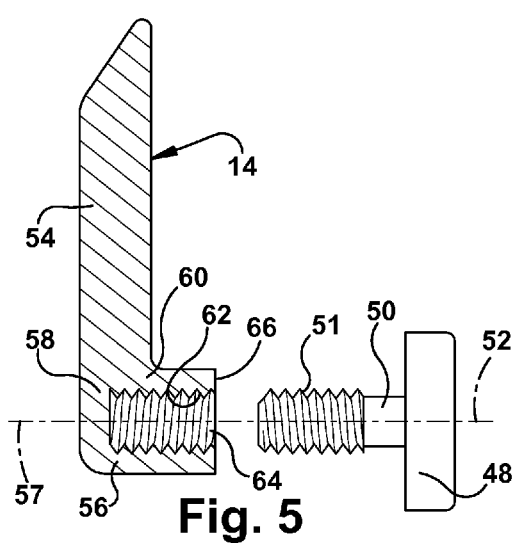
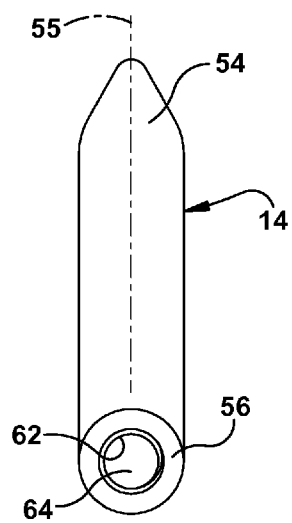

BONE FIXATION APPARATUS AND METHOD

RELATED APPLICATION

This application claims the benefit of U.S. Provisional Patent Application Ser. No. 61/608,185, filed Mar. 8, 2012, the entirety of which is hereby incorporated by reference for all purposes.

FIELD OF THE INVENTION

The present invention relates to a bone fixation apparatus comprising an extramedullary component and an intramedullary component interconnected by a fastener and to a method of using such an apparatus and, more particularly, to a bone fixation apparatus in which a fastener passes through a V-shaped opening formed in an extramedullary component and to a method of using such an apparatus.

BACKGROUND OF THE INVENTION

One method for treating a fractured bone is to apply an internal device to fix the broken pieces of bone in position. Such an internal fixation device may be, for example, a bone plate, bone screw, or nail. When fixing the broken pieces of a bone in position, it is important to align the pieces properly. This may be difficult to accomplish if one or more of the bone pieces is small or displaced from its proper position and the bone fixation device has limited capability for accommodating small or displaced bone pieces.

SUMMARY OF THE INVENTION

The present invention is directed to a bone fixation apparatus comprising an extramedullary component and an intramedullary component interconnected by a fastener and to a method of using such an apparatus and, more particularly, to a bone fixation apparatus in which a fastener passes through a V-shaped opening formed in an extramedullary component and to a method of using such an apparatus.

In accordance with an embodiment of the present invention, a bone fixation apparatus comprises an extramedullary component, an intramedullary component, and a fastener configured and dimensioned to interconnect the extramedullary component and the intramedullary component. The fastener has a head portion and a shank portion. The head portion is configured and dimensioned to be received in the extramedullary component. The shank portion is configured and dimensioned to be received in the intramedullary component. The fastener has a first longitudinal axis extending through both the head portion and the shank portion. The extramedullary component has a second longitudinal axis. The extramedullary component also includes an elongated surface defining an opening through which the shank portion of the fastener passes when the shank portion is received in the intramedullary component. The opening has a V shape. The V shape of the opening is oriented transverse to the first longitudinal axis and to the second longitudinal axis.

In accordance with another embodiment of the present invention, a bone fixation apparatus comprises an extramedullary component and an intramedullary component. The intramedullary component includes a foot portion and a connector portion. The foot portion has a first longitudinal axis. The connector portion has a second longitudinal axis extending transverse to the first longitudinal axis. The bone fixation apparatus also comprises a fastener configured and dimensioned to interconnect the extramedullary component and the intramedullary component. The fastener has a head portion and a shank portion. The head portion is configured and dimensioned to be received in the extramedullary component. The shank portion is configured and dimensioned to be received in the connector portion of the intramedullary component. The fastener has a third longitudinal axis extending through both the head portion and the shank portion. The third longitudinal axis is substantially parallel to the second longitudinal axis when the shank portion is received in the connector portion of the intramedullary component. The extramedullary component has a fourth longitudinal axis and includes an elongated surface defining an elongated opening through which the shank portion of the fastener passes when the shank portion is received in the neck portion of the intramedullary component. The elongated opening has a length. The elongated opening is oriented such that a line extending centrally along the length of the elongated opening is disposed transverse to the first longitudinal axis and to the second longitudinal axis.

In accordance with yet another embodiment of the present invention, a method of using a bone fixation apparatus to fix pieces of a fractured bone comprises the step of providing a bone fixation apparatus. The bone fixation apparatus comprises (i) an extramedullary component, (ii) an intramedullary component, and (iii) a fastener configured and dimensioned to interconnect the extramedullary component and the intramedullary component. The fastener has a head portion and a shank portion. The head portion is configured and dimensioned to be received in the extramedullary component. The shank portion is configured and dimensioned to be received in the intramedullary component. The fastener has a first longitudinal axis extending through both the head portion and the shank portion. The extramedullary component has a second longitudinal axis and includes an elongated surface defining an opening through which the shank portion of the fastener passes when the shank portion is received in the intramedullary component. The opening has a V shape, which is oriented transverse to the first longitudinal axis and to the second longitudinal axis. The method also comprises the steps of inserting a portion of the intramedullary component into an intramedullary portion of a first piece of the bone and positioning the extramedullary component on an extramedullary surface of a second piece of the bone. The method further comprises the steps of inserting the fastener into the opening in the extramedullary component so that the shank portion of the fastener is received in the intramedullary component, and securing the extramedullary component to the second piece of the bone.

BRIEF DESCRIPTION OF THE DRAWINGS

The foregoing and other features and advantages of the present invention will become apparent to one skilled in the art upon consideration of the following description of the invention and the accompanying drawings, in which:

FIG. 3 is a side view of the bone fixation apparatus of FIG. 1 showing the bone in section;

FIG. 4 is an enlarged sectional view of a portion of the bone fixation apparatus of FIG. 3;

FIG. 5 is an exploded sectional view of two components of the bone fixation apparatus of FIG. 4;

FIG. 6 is a top view of one of the components of FIG. 5;

DETAILED DESCRIPTION

Figure 1:
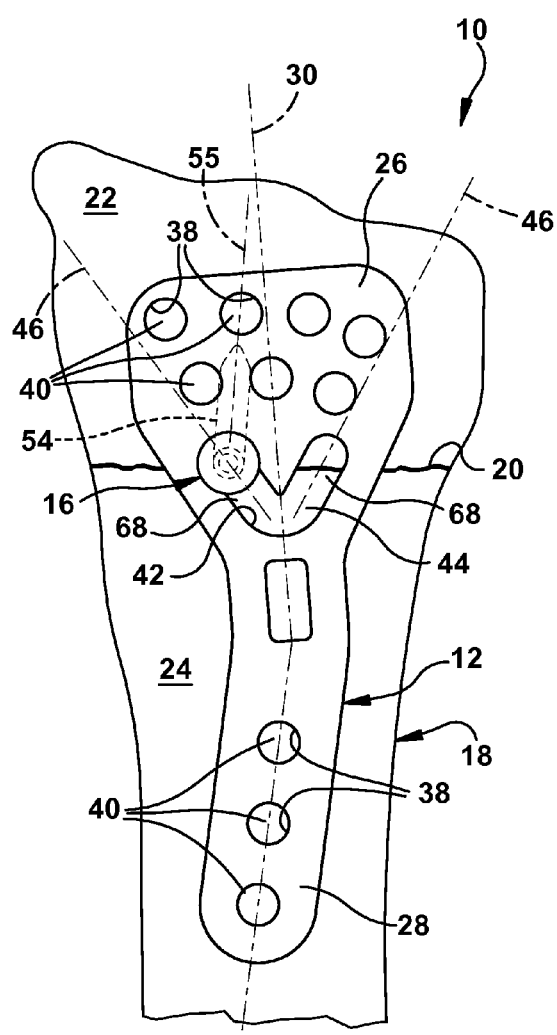
FIG. 1 is a top view of a bone fixation apparatus, in accordance with an embodiment of the present invention, applied to a fractured bone.

FIGS. 1 through 6 illustrate a bone fixation apparatus 10 in accordance with an example of the present invention. The bone fixation apparatus 10 includes an extramedullary component or bone plate 12, an intramedullary component or flange 14, and a fastener 16. As shown in FIGS. 1 through 4, the bone fixation apparatus 10 may be applied to a bone 18 to reduce and stabilize a fracture 20 in the bone. In the bone 18, the fracture 20 has caused the bone to separate into an end bone piece 22, which includes a condylar portion of the bone, and a tubular long bone piece 24.

The bone plate 12 is made of a relatively rigid bio-compatible material, such as medical grade stainless steel or titanium. The bone plate 12 includes an enlarged head portion 26 and an elongated tail portion 28. A central longitudinal axis 30 of the bone plate 12 extends through the head portion 26 and the tail portion 28. An inward facing first surface 32 of the bone plate 12 extends longitudinally of the bone plate and is configured to be presented toward an external surface 34 of the bone 18. An opposite, outward facing second surface 36 of the bone plate 12 extends longitudinally of the bone plate and is configured to be presented away from the external surface 34 of the bone 18. The first and second surfaces 32 and 36 of the bone plate 12 are spaced apart by a distance that is the thickness of the bone plate. The inward facing first surface 32 of the bone plate 12 may have a flat configuration, concavely curved configuration, or a complex configuration to conform more closely to the configuration of the external surface 34 of the bone 18. The head portion 26 of the bone plate 12 is wider than the tail portion 28 so as to provide a larger width for contacting the end bone piece 22, which is wider than the long bone piece 24.

Both the head portion 26 and the tail portion 28 of the bone plate 12 include surfaces 38 that define openings 40 formed in the bone plate 12. The openings 40 extend from the inward facing first surface 32 entirely through the bone plate 12 to the outward facing second surface 36. The openings 40 are configured to receive fasteners (not shown), such as bone screws, to help secure the bone plate 12 to the bone 18.

In addition to surfaces 38 and openings 40, the head portion 26 of the bone plate 12 includes an elongated, V-shaped surface 42 that defines an elongated, V-shaped opening 44. The V-shaped opening 44 extends from the inward facing first surface 32 entirely through the bone plate 12 to the outward facing second surface 36. The V-shaped opening 44 has a V-shaped central longitudinal axis 46 and is dimensioned and configured to receive the fastener 16. The central longitudinal axis 46 of the V-shaped opening 44 is oriented transverse to the central longitudinal axis 30 of the bone plate 12. More particularly, the central longitudinal axis 30 of the bone plate 12 intersects the central longitudinal axis 46 of the V-shaped opening 44 at about the apex of the V shape of the central longitudinal axis 46. As a result, the two arms 68 of the V-shaped opening 44 are disposed on opposite sides of the central longitudinal axis 30 of the bone plate 12.

The fastener 16 is configured and dimensioned to interconnect the bone plate 12 and the flange 14. As shown in FIG. 5, the fastener 16 has an enlarged head portion or head 48 and an elongated shaft portion or shaft 50. The fastener 16 is made of a relatively rigid bio-compatible material, such as medical grade stainless steel or titanium. The shaft 50 has an external surface 51 that is threaded. A central longitudinal axis 52 of the fastener 16 extends through both the head 48 and the shaft 50. The V-shaped opening 44 and head 48 and shaft 50 of the fastener 16 are configured and dimensioned such that the shaft 50 can pass through the V-shaped opening 44, but the head 48 cannot pass through the V-shaped opening.

As best shown in FIG. 4, the fastener 16 engages the flange 14. The flange 14 is made of a relatively rigid bio-compatible material, such as medical grade stainless steel or titanium. The flange 14 includes an elongated foot portion or foot 54 and a shorter connector portion or connector 56. The foot 54 has a central longitudinal axis 55. One end 58 of the foot 54 is joined to an end 60 of the connector 56. As shown, the foot 54 is formed in one piece with the connector 56. The connector 56 has a central longitudinal axis 57 and is oriented at an angle, such as 90°, with respect to the foot 54. The connector 56 includes an internal surface 62 that is threaded. The threaded internal surface 62 defines a passage 64 that extends lengthwise of the connector 56 toward the foot 54 from an end 66 of the connector opposite the end 60. The passage 64 is dimensioned to receive the shaft 50 of the fastener 16 so that the threaded external surface 51 of the shaft engages the threaded internal surface 62 of the connector 56 and so that the fastener can be screwed into the connector.

The bone plate 12, the flange 14, and the fastener 16 of the bone fixation apparatus 10 are assembled together by inserting the shaft 50 of the fastener into the V-shaped opening 44 of the bone plate. When the shaft 50 is inserted into the V-shaped opening 44, the central longitudinal axis 52 of the fastener 16 is coaxial with and, therefore, coincident with the central longitudinal axis 57 of the connector 56. In addition, the head 48 of the fastener 16 abuts the outward facing second surface 36 of the bone plate 12. The shaft 50 of the fastener 16 is received in and passes through the V-shaped opening 44 in the bone plate. The shaft 50 is then screwed into the connector 56 of the flange 14 so that the threaded external surface 51 of the shaft engages the threaded internal surface 62 of the connector.

When the bone plate 12, the flange 14, and the fastener 16 are assembled together, the flange is disposed entirely on one side of the bone plate and does not project beyond the inward facing first surface 32 of the bone plate in a direction toward the outward facing second surface 36 or in any other direction. In addition, the foot 54 of the flange is spaced apart from the bone plate 12. The foot 54 may extend generally parallel to the bone plate, depending upon the angle between the connector 56 and the foot 54 of the flange. Further, the central longitudinal axis 46 of the V-shaped opening 44 is oriented transverse to the central longitudinal axis 52 of the fastener 16.

In use, the desired placement of the bone plate 12 and the flange 14 is first determined. For example, the bone plate 12 of the bone fixation apparatus 10 is placed against an external surface of a fractured bone. With particular reference to FIGS. 1-4, the bone plate 12 is placed against the bone 18 such that the inward facing first surface 32 of the bone plate contacts the external surface 34 of the bone. The position of the bone plate 12 is then adjusted to facilitate attachment of the bone plate to the bone pieces 22 and 24 and to facilitate desired placement of the flange 14. For example, as shown in FIG. 1, the bone plate 12 may be positioned so that one of the two arms 68 of the V-shaped opening 44 overlies the fracture 20 in the bone 18. In other words, one of the two arms 68 of the V-shaped opening 44 may be positioned so that it lies or extends above the fracture 20. While lying or extending above the fracture 20, the arm 68 also lies or extends either (a) across or transverse to the fracture or (b) generally parallel to or along the fracture. Such positioning allows the foot 54 of the flange 14 to be inserted into the intramedullary portion 70 of the end bone piece 22 at the fracture 20 and also allows the connector 56 to extend through a portion of the fracture to the V-shaped opening 44, all as shown in FIG. 3.

At the same time as or before or after the desired position of the bone plate 12 is selected or determined, the position of the flange 14 is selected or determined. The flange 14 is positioned relative to the end bone piece 22 such that the foot 54 of the flange will effectively engage the intramedullary portion 70 of the end bone piece. The associated position of the flange 14 along the V-shaped opening 44 and the angular orientation of the foot 54 of the flange relative to the V-shaped opening and the bone plate are also selected or determined. The positioning of the bone plate 12 and the flange 14 will effectively result in a particular relative angular orientation of the central longitudinal axis 30 of the bone plate 12 and the central longitudinal axis 55 of the foot 54 of the flange. The positioning of the bone plate 12 and the flange 14 will also effectively result in a particular relative angular orientation of the central longitudinal axis 55 of the foot 54 of the flange and the central longitudinal axis 46 of the V-shaped opening 44.

After the desired positions of the bone plate 12 and the flange 14 are selected or determined, the bone plate and the flange may be moved to allow the bone 18 to be drilled and/or otherwise prepared to receive the bone plate and the flange. After the bone 18 has been prepared, the bone plate 12 and the flange 14 are moved to their desired positions and the fastener 16 is installed to attach the flange to the bone plate. Specifically, the foot 54 of the flange 14 is inserted into the intramedullary portion 70 of the end bone piece 22. The inward facing first surface 32 of the bone plate 12 is positioned in contact with or abutting the external surface 34 of the bone piece 24. When the flange 14 is in its desired position and angular orientation with respect to the bone 18, the bone plate 12, and the V-shaped opening 44, the fastener 16 is screwed into the connector 56 of the flange using an appropriate tool (not shown) that engages the head 48 of the flange.

As the fastener 16 is advanced or screwed into the connector 56, the bone plate 12 and the foot 54 of the flange 14 are drawn toward each other and toward the cortical portion 72 of the bone 18. The relative movement of the bone plate 12 and the foot 54 of the flange 14 toward each other will tend to clamp the cortical portion 72 of the bone 18 between the bone plate and the foot of the flange. Depending upon the thickness of the cortical portion 72 of the bone 18 and the length of the connector 56, the end 66 of the connector opposite the foot 54 may abut or contact the inward facing first surface 32 of the bone plate 12. When the desired relationship between the flange 14, the bone plate 12, and the cortical portion 72 of the bone 18 has been achieved, the bone plate 12 may be further secured to the bone 18 by inserting one or more bone screws (not shown) into one or more of the openings 40 in the bone plate 12 and into one or both of the bone pieces 22 and 24.

Although the desired positions of the bone plate 12 and the flange 14 may be selected or determined as set out above, it may be necessary to adjust the desired positions during installation or implantation of the bone plate and/or the flange. In this regard, the V shape of the V-shaped opening 44 may be particularly beneficial. Specifically, the V shape allows lateral and/or longitudinal adjustments of the position of the flange 14 relative to the bone 18 without requiring identical movements of the bone plate 12. Thus, it may be possible, during installation or implantation of the bone plate 12 and flange 14, for example, to move the flange 14 either laterally or longitudinally relative to the bone 18 with little or no movement of the bone plate 12. In addition, it is possible to adjust the angular orientation of the flange 14 and the bone plate by rotating or pivoting the foot 54 of the flange about the central longitudinal axis 57 of the connector 56. Thus, the relative angular orientation of the central longitudinal axis 30 of the bone plate 12 and the central longitudinal axis 55 of the foot 54 of the flange may be adjusted, and the relative angular orientation of the central longitudinal axis 55 of the foot 54 of the flange and the central longitudinal axis 46 of the V-shaped opening 44 may also be adjusted.

Although the bone fixation apparatus 10 is shown in FIGS. 1-4 as having only three components and being applied to the bone 18 in a particular position and orientation, other constructions and bone applications of the bone fixation apparatus are possible. For example, the bone plate 12 may be positioned so that both arms 68 of the V-shaped opening 44 overlie the fracture 20 in the bone 18. In other words, both arms 68 of the V-shaped opening 44 may be positioned so that they both lie or extend above the fracture 20. While lying or extending above the fracture 20, the arms 68 would also lie or extend either (a) across or transverse to the fracture or (b) generally parallel to or along the fracture. Such positioning would permit the use of a second flange 14 (not shown) attached to the bone plate 12 by a second fastener 16 (not shown). The use of two flanges 14 may help retain the end bone piece 22 or may help retain a second end bone piece (not shown). Depending upon the length of the V-shaped opening 44, more than two flanges 14 and fasteners 16 may be used to help retain one or more end bone pieces.

Similarly, the foot 54 of the flange 14 is shown in FIGS. 1-6 as having a particular length relative to the bone pieces 22 and 24 and the bone plate 12. This relative length may be varied so that foot 54 of the flange 14 is longer or shorter than shown in FIGS. 1-6. The foot 54 may also extend at an angle relative to the connector 56 that is different from the angle shown in FIGS. 1-6 in order to accommodate, for example, variations in the thickness of the cortical portion 72 of the bone 18. The connector 56 may be joined to the foot 54 at a location different than the end 58 of the foot, such as the mid-point of the length of the foot. The connector 56 may also be joined to two or more feet 54, which may be oriented at different angles to each other and to the connector. The length of the connector 56 may vary from the relative length shown in FIGS. 1-6 to accommodate, for example, variations in the thickness of the cortical portion 72 of the bone 18. The flange 14 may also have more than one foot 54.

Figure 2:
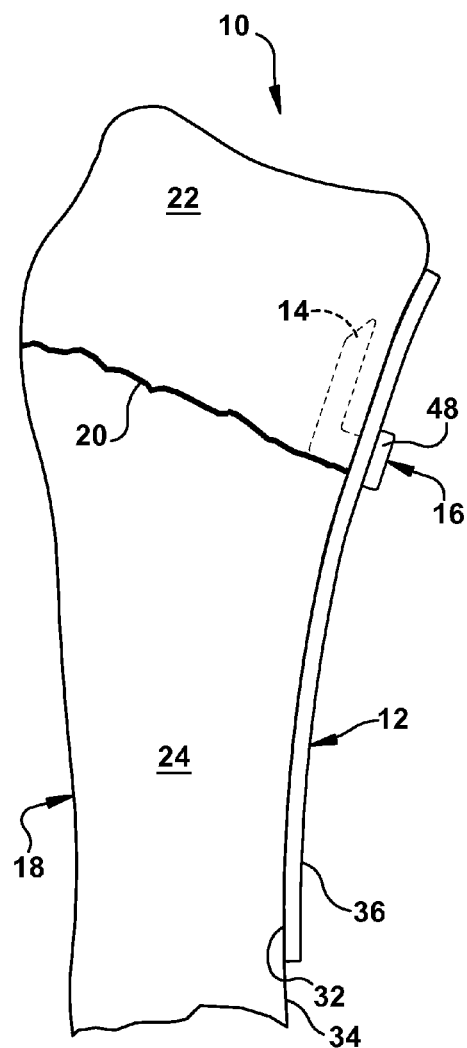
FIG. 2 is a side view of the bone fixation apparatus of FIG. 1.
Figure 7:
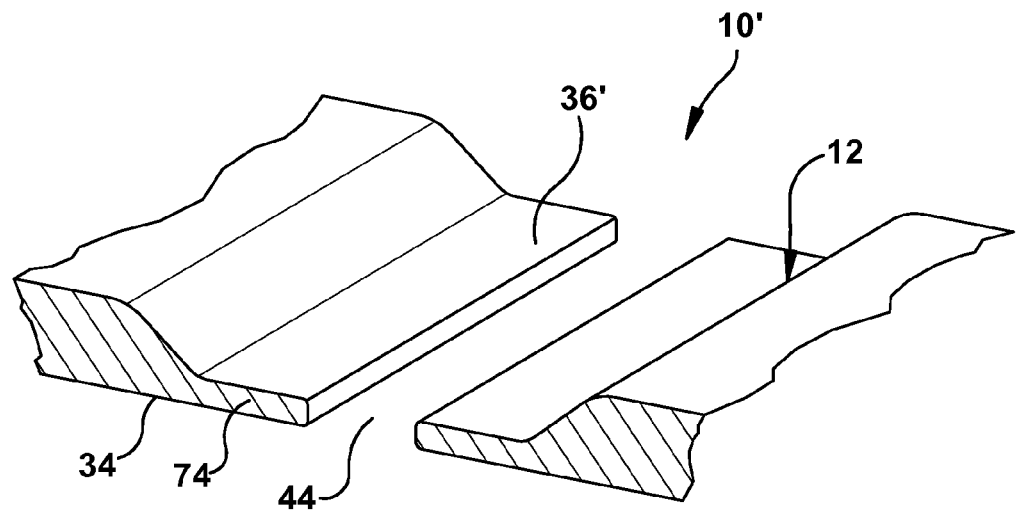
FIG. 7 is an enlarged view of a portion of one component of a bone fixation apparatus in accordance with a second embodiment of the present invention.
Figure 8:
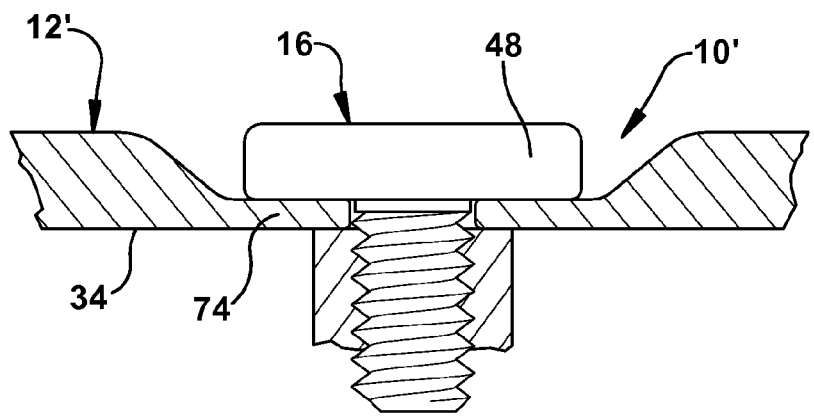
FIG. 8 is an enlarged sectional view of portions of three components of the bone fixation apparatus in accordance with the second embodiment of the present invention.

Further, although FIGS. 2-3 show the head 48 of the fastener 16 projecting above all portions of the outward facing second surface 36 of the bone plate 12, a less obtrusive interengagement of the fastener and the bone plate may be employed. For example, FIGS. 7-8 show a bone fixation apparatus 10' in accordance with a second embodiment of the present invention, in which a portion of the outward facing second surface 36' of the bone plate 12' adjacent to the elongated V-shaped opening 44 is configured to be closer to the inward facing first surface 32 than portions of the second surface that are farther from the V-shaped opening. The width of the resulting reduced thickness portion 74 of the bone plate 12' is approximately equal to or slightly wider than the largest diameter of the head 48 of the fastener 16. As a consequence, when the head 48 of the fastener 16 contacts or abuts the outward facing second surface 36' of the reduced thickness portion 74 of the bone plate 12', the head either projects not all above most of the outward facing surface of the bone plate or projects to a much lesser above most of the outward facing Having described the invention, the following is claimed:

1. A bone fixation apparatus comprising:
    an extramedullary component;
    an intramedullary component; and
    a fastener configured and dimensioned to interconnect the extramedullary component and the intramedullary component,
    the fastener having a head portion and a shank portion, the head portion being configured and dimensioned to be received in the extramedullary component,
    the shank portion being configured and dimensioned to be received in the intramedullary component, the fastener having a first longitudinal axis extending through both the head portion and the shank portion,
    the extramedullary component having a second longitudinal axis, the extramedullary component also having a longitudinally extending first surface and a longitudinally extending second surface spaced apart from the first surface by a thickness of the extramedullary component, the extramedullary component including an elongated surface extending transverse to the first and second surfaces and defining an opening through which the shank portion of the fastener passes when the shank portion is received in the intramedullary component, the opening having a V shape, the entire V-shaped opening extending from the first surface through the extramedullary component to the second surface, the V shape being oriented transverse to the first longitudinal axis and to the second longitudinal axis,
    the intramedullary component comprising a foot portion and a connector portion, the intramedullary component having an overall L shape, the foot portion forming a first leg of the L shape and the connector portion forming a second leg of the L shape, the foot portion having a third longitudinal axis, the connector portion having a fourth longitudinal axis extending transverse to the third longitudinal axis, the shank portion of the fastener being received in and engaged with the connector portion of the intramedullary component and the first longitudinal axis being substantially coaxial with the fourth longitudinal axis when the shank portion of the fastener is received in the intramedullary component.

2. A bone fixation apparatus according to claim 1, wherein the first longitudinal axis is a central longitudinal axis of the shank portion of the fastener, and the fourth longitudinal axis is a central longitudinal axis of the connector portion.

3. A bone fixation apparatus according to claim 1, wherein the third longitudinal axis has an orientation relative to the second longitudinal axis, the orientation of the third longitudinal axis relative to the second longitudinal axis being adjustable by rotating the foot portion of the intramedullary component about the fourth longitudinal axis when the head portion of the fastener is received in the extramedullary component and the shank portion of the fastener is received in the intramedullary component.

4. A bone fixation apparatus according to claim 1, wherein the foot portion of the intramedullary component is spaced apart from the extramedullary component when the shank portion of the fastener is received in the connector portion of the intramedullary component.

5. A bone fixation apparatus according to claim 1, wherein a first portion of the second surface adjacent to the opening is spaced apart from the first surface by a first distance, the first portion of the second surface being disposed between the opening and a second portion of the second surface, the second portion of the second surface being spaced apart from the first surface by a second distance, the second distance being larger than the first distance.

6. The bone fixation device of claim 1, wherein the bone fixation device is configured to extend from an intramedullary portion of a first bone piece, across a bone fracture, and into an intramedullary canal of a second bone piece.

7. A bone fixation apparatus comprising:
    an extramedullary component;
    an intramedullary component comprising a foot portion and a connector portion, the foot portion having a first longitudinal axis, the connector portion having a second longitudinal axis extending transverse to the first longitudinal axis, the connector portion being a tubular member and the second longitudinal axis being a central longitudinal axis of the connector portion; and
    a fastener configured and dimensioned to interconnect the extramedullary component and the intramedullary component, the fastener having a head portion and a shank portion, the head portion being configured and dimensioned to be received in and engaged with the extramedullary component, the shank portion being configured and dimensioned to be received in the connector portion of the intramedullary component, the fastener having a third longitudinal axis extending through both the head portion and the shank portion, the third longitudinal axis being substantially coaxial with the second longitudinal axis when the shank portion is received in the connector portion of the intramedullary component,
    the extramedullary component having a fourth longitudinal axis and including an elongated surface defining an elongated opening through which the shank portion of the fastener passes when the shank portion is received in the connector portion of the intramedullary component, the elongated opening having a length, the elongated opening being oriented such that a line extending centrally along the length of the elongated opening is disposed transverse to the first longitudinal axis and to the second longitudinal axis.

8. A bone fixation apparatus according to claim 7, wherein the elongated opening is V shaped.

9. A bone fixation apparatus according to claim 7, wherein the first longitudinal axis has an orientation relative to the fourth longitudinal axis, the orientation of the first longitudinal axis relative to the fourth longitudinal axis being adjustable by rotating the foot portion of the intramedullary component about the second longitudinal axis when the head portion of the fastener is received in the extramedullary component and the shank portion of the fastener is received in the intramedullary component.

10. A bone fixation apparatus according to claim 7, wherein the intramedullary component has an overall L shape, the foot portion forming a first leg of the L shape and the connector portion forming a second leg of the L shape, the shank portion of the fastener being engaged with the connector portion of the intramedullary component when the shank portion of the fastener is received in the intramedullary component.

11. A bone fixation apparatus comprising:
    an extramedullary component;
    an intramedullary component comprising a foot portion and a connector portion, the foot portion having a first longitudinal axis, the connector portion having a second longitudinal axis extending transverse to the first longitudinal axis, the second longitudinal axis intersecting the first longitudinal axis such that an intersection between the first and second longitudinal axes is disposed within the intramedullary component; and a fastener configured and dimensioned to interconnect the extramedullary component and the intramedullary component, the fastener having a head portion and a shank portion, the head portion being configured and dimensioned to be received in the extramedullary component, the shank portion being configured and dimensioned to be received in the connector portion of the intramedullary component, the fastener having a third longitudinal axis extending through both the head portion and the shank portion, the third longitudinal axis being substantially coaxial with the second longitudinal axis when the shank portion is received in the connector portion of the intramedullary component, the extramedullary component having a fourth longitudinal axis and including an elongated surface defining an elongated opening through which the shank portion of the fastener passes when the shank portion is received in the connector portion of the intramedullary component, the elongated opening having a length, the elongated opening being oriented such that a line extending centrally along the length of the elongated opening is disposed transverse to the first longitudinal axis and to the second longitudinal axis.

12. A bone fixation apparatus according to claim 11, wherein the intramedullary component has an overall L shape, the foot portion forming a first leg of the L shape and the connector portion forming a second leg of the L shape, the shank portion of the fastener being engaged with the connector portion of the intramedullary component when the shank portion of the fastener is received in the intramedullary component.

* * * * *